(12) United States Patent
Hopkins et al.

(10) Patent No.: US 8,992,623 B2
(45) Date of Patent: *Mar. 31, 2015

(54) SHOULDER PROSTHESIS

(75) Inventors: Andrew Hopkins, Winterthur (CH); Levent Kusogullari, Winterthur (CH)

(73) Assignee: Zimmer GmbH, Winterthur (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/006,376

(22) PCT Filed: Feb. 15, 2012

(86) PCT No.: PCT/EP2012/052627
§ 371 (c)(1),
(2), (4) Date: Dec. 17, 2013

(87) PCT Pub. No.: WO2012/130524
PCT Pub. Date: Oct. 4, 2012

(65) Prior Publication Data
US 2014/0107792 A1    Apr. 17, 2014

(30) Foreign Application Priority Data
Mar. 25, 2011 (EP) ..................... 11002505

(51) Int. Cl.
*A61F 2/40* (2006.01)
*A61F 2/30* (2006.01)

(52) U.S. Cl.
CPC ..... *A61F 2/4003* (2013.01); *A61F 2002/30163* (2013.01); *A61F 2002/30777* (2013.01);
(Continued)

(58) Field of Classification Search
CPC ....... A61F 2/40; A61F 2/2601; A61F 2/4603; A61F 2002/4003; A61F 2002/4007; A61F 2002/30841; A61F 2002/30845; A61F 2002/30848; A61F 2002/30891; A61F 2002/30894; A61F 2002/30896; A61F 2002/30899; A61F 2002/30901; A61F 2002/30902

USPC .......... 623/19.11, 19.13, 19.14, 22.23, 22.32, 623/22.38, 23.11, 23.12, 23.42, 23.43
See application file for complete search history.

(56) References Cited

U.S. PATENT DOCUMENTS 4,035,848 A   7/1977 Wagner
4,042,980 A   8/1977 Swanson et al.
(Continued)

FOREIGN PATENT DOCUMENTS

DE   1164019 B    2/1964
DE   19803183 A1  8/1999
(Continued)

OTHER PUBLICATIONS

"U.S. Appl. No. 13/428,441, Advisory Action mailed Oct. 8, 2013", 2 pgs.
(Continued)

*Primary Examiner* — Randy Shay
(74) *Attorney, Agent, or Firm* — Schwegman Lundberg & Woessner, P.A.

(57) ABSTRACT

The present disclosure relates to a stemless shoulder prosthesis comprising a fixation device for fixing the prosthesis to a resected humerus bone, the fixation device comprising a base portion (11, 31, 32) and anchoring means (12, 12'), the base portion (11, 31, 32) having a distal side adapted to contact a resection plane of the bone and a proximal side for carrying a humeral head. The anchoring means (12, 12') are connected to the distal side of the base portion (11, 31, 32) and adapted to fix the prosthesis to the bone. The anchoring means (12, 12') define a central axis (C), wherein the anchoring means (12, 12') comprise a plurality of protrusions (13, 13', 13a, 13b, 13c) projecting from the base portion (11, 31, 32), each protrusion (13, 13', 13a, 13b, 13c) extending between an inner end (I) and an outer end (O). The protrusions (13, 13', 13a, 13b, 13c) define a free central space (F) around the central axis (C).

20 Claims, 5 Drawing Sheets

Figure 1:
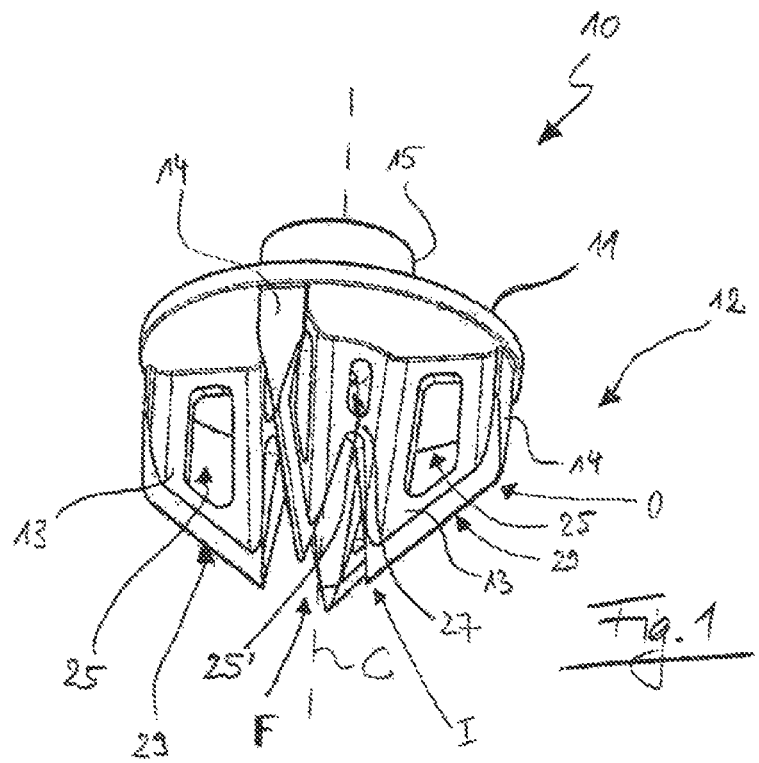

(52) U.S. Cl.
CPC .......... *A61F2002/30848* (2013.01); *A61F 2002/30884* (2013.01); *A61F 2002/30889* (2013.01); *A61F 2002/30892* (2013.01); *A61F 2002/30902* (2013.01)
USPC .......... 623/19.11; 623/19.14; 623/23.12

(56) References Cited

U.S. PATENT DOCUMENTS

| | | | |
|---|---|---|---|
| 4,332,036 | A | 6/1982 | Sutter et al. |
| 4,470,158 | A | 9/1984 | Pappas et al. |
| 4,550,450 | A | 11/1985 | Kinnett |
| 4,964,865 | A | 10/1990 | Burkhead et al. |
| 4,986,833 | A | 1/1991 | Worland |
| 5,032,132 | A | 7/1991 | Matsen, III et al. |
| 5,250,050 | A | 10/1993 | Poggie et al. |
| 5,271,737 | A | 12/1993 | Baldwin et al. |
| 5,314,479 | A | 5/1994 | Rockwood, Jr. et al. |
| 5,358,526 | A | 10/1994 | Tornier |
| 5,403,320 | A | 4/1995 | Luman et al. |
| 5,489,309 | A | 2/1996 | Lackey et al. |
| 5,571,203 | A | 11/1996 | Masini |
| 5,665,090 | A | 9/1997 | Rockwood et al. |
| 5,957,979 | A | 9/1999 | Beckman et al. |
| 6,146,423 | A | 11/2000 | Cohen et al. |
| 6,168,630 | B1 | 1/2001 | Keller et al. |
| 6,334,874 | B1 | 1/2002 | Tornier et al. |
| 6,783,549 | B1 | 8/2004 | Stone et al. |
| 7,465,319 | B2 | 12/2008 | Tornier |
| 7,615,080 | B2 | 11/2009 | Ondrla |
| 7,670,382 | B2 | 3/2010 | Parrott et al. |
| 7,678,150 | B2 | 3/2010 | Tornier et al. |
| 7,887,544 | B2 | 2/2011 | Tornier et al. |
| D643,926 | S | 8/2011 | Collins |
| 8,187,282 | B2 | 5/2012 | Tornier et al. |
| 8,192,497 | B2 | 6/2012 | Ondrla |
| 8,231,682 | B2 | 7/2012 | Lafosse et al. |
| 8,246,687 | B2 | 8/2012 | Katrana et al. |
| 2001/0047210 | A1 | 11/2001 | Wolf |
| 2003/0028253 | A1 | 2/2003 | Stone et al. |
| 2003/0153918 | A1 | 8/2003 | Putnam et al. |
| 2007/0054553 | A1 | 3/2007 | Nishio et al. |
| 2007/0142917 | A1 | 6/2007 | Roche et al. |
| 2007/0162149 | A1 | 7/2007 | Kropf et al. |
| 2008/0221700 | A1 | 9/2008 | Howald et al. |
| 2009/0048681 | A1 | 2/2009 | Vlachos |
| 2010/0114326 | A1 | 5/2010 | Winslow et al. |
| 2012/0265315 | A1 | 10/2012 | Kusogullari et al. |
| 2012/0296435 | A1 | 11/2012 | Ambacher |

FOREIGN PATENT DOCUMENTS

| | | | |
|---|---|---|---|
| EP | 0013864 | A1 | 8/1980 |
| EP | 0485326 | A1 | 5/1992 |
| EP | 0577529 | A1 | 1/1994 |
| EP | 1467681 | B1 | 2/2008 |
| FR | 2691355 | A1 | 11/1993 |
| FR | 2304324 | A1 | 10/1996 |
| WO | WO-0217822 | A1 | 3/2002 |
| WO | WO-2007054553 | A1 | 5/2007 |
| WO | WO-2012130524 | A1 | 10/2012 |

OTHER PUBLICATIONS

"U.S. Appl. No. 13/428,441, Examiner Interview Summary mailed Jul. 23, 2013", 3 pgs.
"U.S. Appl. No. 13/428,441, Final Office Action mailed Jul. 25, 2013", 10 pgs.
"U.S. Appl. No. 13/428,441, Non Final Office Action mailed Nov. 5, 2013", 8 pgs.
"U.S. Appl. No. 13/428,441, Non Final Office Action mailed Dec. 28, 2012", 10 pgs.
"U.S. Appl. No. 13/428,441, Preliminary Amendment filed Mar. 23, 2012", 5 pgs.
"U.S. Appl. No. 13/428,441, Response filed Jun. 28, 2013 to Non Final Office Action mailed Dec. 28, 2012", 8 pgs.
"U.S. Appl. No. 13/428,441, Response filed Sep. 25, 2013 to Final Office Action mailed Jul. 25, 2013", 8 pgs.
"U.S. Appl. No. 13/428,446, Advisory Action mailed Oct. 7, 2013", 2 pgs.
"U.S. Appl. No. 13/428,446, Examiner Interview Summary mailed Jul. 23, 2013", 3 pgs.
"U.S. Appl. No. 13/428,446, Final Office Action mailed Jul. 25, 2013", 9 pgs.
"U.S. Appl. No. 13/428,446, Non Final Office Action mailed Nov. 1, 2013", 8 pgs.
"U.S. Appl. No. 13/428,446, Non Final Office Action mailed Dec. 28, 2012", 10 pgs.
"U.S. Appl. No. 13/428,446, Preliminary Amendment filed Mar. 23, 2012", 5 pgs.
"U.S. Appl. No. 13/428,446, Response filed Jun. 28, 2013 to Non Final Office Action mailed Dec. 28, 2012", 3 pgs.
"U.S. Appl. No. 13/428,446, Response filed Sep. 25, 2013 to Final Office Action mailed Jul. 25, 2013", 7 pgs.
"U.S. Appl. No. 29/413,611, Response filed Nov. 4, 2013 to Restriction Requirement mailed Oct. 4, 2013", 8 pgs.
"U.S. Appl. No. 29/413,610, Response filed Nov. 4, 2013 to Restriction Requirement mailed Oct. 4, 2013", 9 pgs.
"U.S. Appl. No. 29/413,610, Restriction Requirement mailed Oct. 4, 2013", 7 pgs.
"U.S. Appl. No. 29/413,611, Restriction Requirement mailed Oct. 4, 2013", 7 pgs.
"European Application Serial No. 12155644.3, European Search Report mailed May 2, 2012", 4 pgs.
"European Application Serial No. 12155645.0, European Search Report mailed May 2, 2012", 4 pgs.
"International Application Serial No. PCT/EP2012/052627, International Preliminary Report on Patentability mailed Mar. 8, 2013", 11 pgs.
"International Application Serial No. PCT/EP2012/052627, International Search Report and Written Opinion mailed May 4, 2012", 5 pgs.
"U.S. Appl. No. 13/428,441, Notice of Allowance mailed Apr. 2, 2014", 8 pgs.
"U.S. Appl. No. 13/428,441, Response filed Feb. 5, 2014 to Non-Final Office Action dated Nov. 5, 2013", 8 pgs.
"U.S. Appl. No. 13/428,446, Notice of Allowance mailed Apr. 1, 2014", 9 pgs.
"U.S. Appl. No. 13/428,446, Response filed Feb. 6, 2014 to Non Final Office Action mailed Nov. 1, 2013", 8 pgs.
"U.S. Appl. No. 29/413,610, Non Final Office Action mailed Dec. 20, 2013", 7 pgs.
"U.S. Appl. No. 29/413,610, Response filed Mar. 20, 2014 to Non-Final Office Action mailed Dec. 20, 2013", 5 pgs.

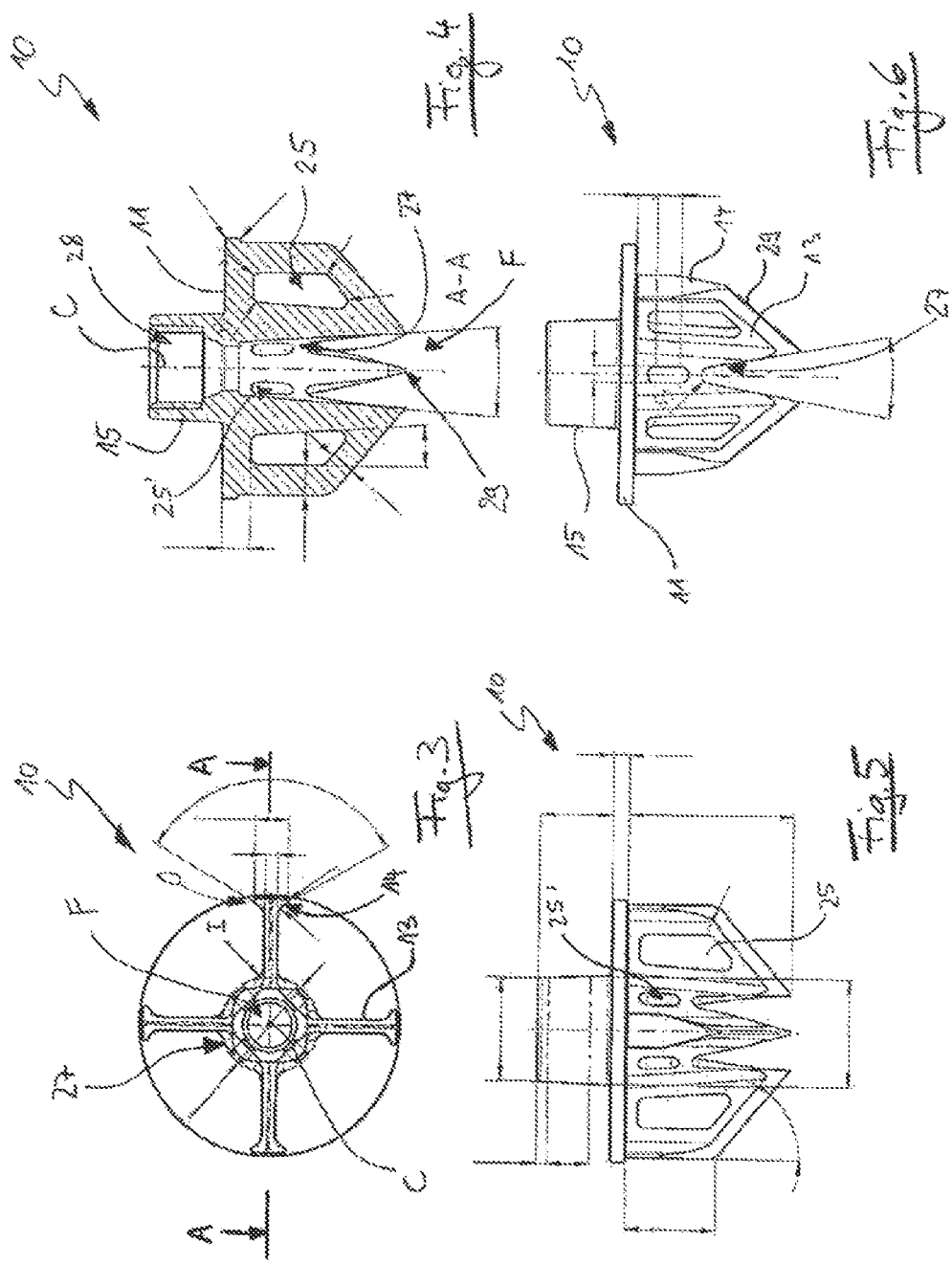

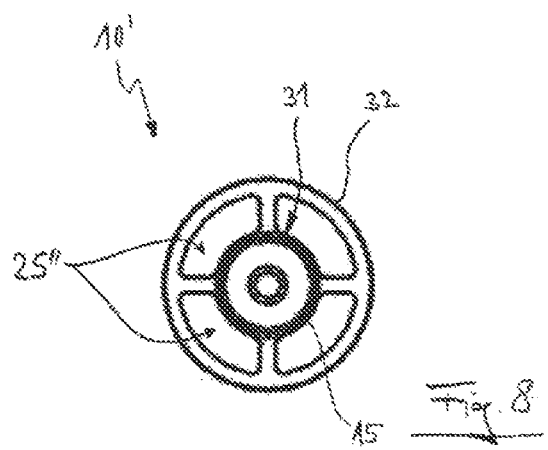
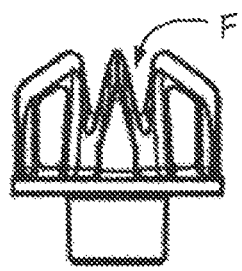
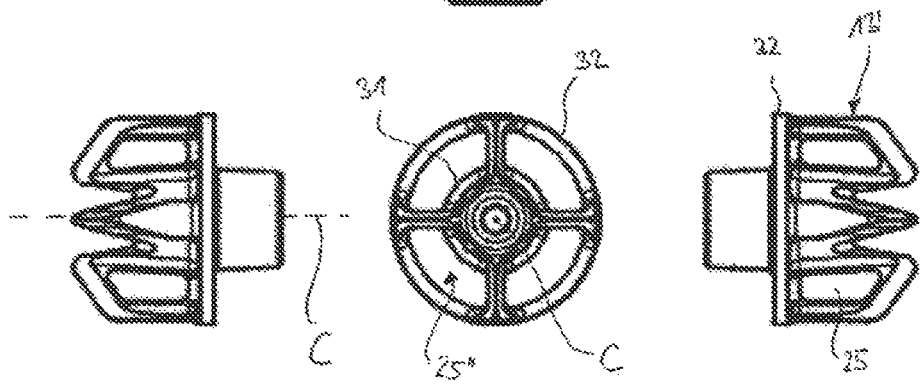
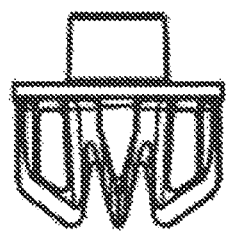

SHOULDER PROSTHESIS

The present disclosure relates to a stemless shoulder prosthesis.

CLAIM OF PRIORITY

This patent application is a U.S. National Stage Filing under 35 U.S.C. §371 of International Patent Application Serial No. PCT/EP2012/052627, filed on Feb. 15, 2012 and published on Oct. 4, 2012 as WO 2012/130524 A1, which claims benefit of priority of European Application No. 11002505.3, filed on Mar. 25, 2011, the benefit of priority of each of which is claimed hereby and each of which is incorporated by reference herein in its entirety.

Generally, a stemless shoulder prosthesis comprises a metaphysical fixation device for fixing the prosthesis to a resected humerus bone. The fixation device comprises a base portion and anchoring means, with a humeral head being fixed to the base portion, for example through a taper or screw connection.

Unlike shoulder prostheses having a stem, also referred to as stemmed shoulder prostheses, stemless shoulder prostheses do not make use of the humeral canal in the diaphysis of the humerus. In other words, stemless shoulder prostheses do not rely on their fixation in said canal and an anchoring means extending deep into said canal is therefore not provided. This bears the advantage that it is in general not necessary to prepare the humeral canal for the insertion of the prosthesis and consequently bone is conserved.

In EP 1 467 681 a shoulder joint endoprosthesis is disclosed which, while fixation is largely limited to the epiphyseal region of the humerus, relies on a short central stem for fixation within the bone. Any ribs or fins solely are described as a torsional safeguard while fixation is achieved through a short tapered stem.

The present disclosure relates to a stemless shoulder prosthesis having a specifically designed fixation device. In particular, combinations of specific base portion designs and anchoring means are described.

According to the present disclosure, the base portion has a distal side adapted to contact a resection plane of the humerus bone and a proximal side for carrying a humeral head. The anchoring means are connected to the distal side of the base portion and are adapted to fix the prosthesis to the bone. The anchoring means define a central axis and comprise a plurality of protrusions projecting from the base portion, each protrusion extending between an inner end and an outer end. The protrusions define a free central space around the central axis.

In other words, the protrusions are arranged around the free central space and said free central space is not provided with protrusions or stem-like anchoring means. In an implanted state of the prosthesis, bony material of the humerus bone can penetrate the free central space and contribute to the anchoring of the prosthesis in the bone.

In this context, the terms "inner end" and "outer end" are to be understood such that the "inner end" has a smaller distance from the central axis than the corresponding "outer end". The protrusions may extend not exclusively into a radial direction but may have an extension component in a circumferential direction, may be curved or may extend in a linear, non-radial direction.

In an embodiment of the prosthesis according to the present disclosure, the inner ends of the protrusions define the free central space. The inner ends may be the radially inner endpoints or edges of the protrusions. Alternatively, radially inner segments of the protrusions may be construed as inner ends in the above sense. In particular, portions of the protrusion which are arranged closest to the central axis define the free central space.

In an embodiment of the prosthesis according to the present disclosure, the anchoring means may comprise exclusively the plurality of protrusions. However, if needed additional means for anchoring the prosthesis may be provided.

In particular, the central axis and/or the protrusions extend or project generally perpendicular to the distal side of the base portion. Additionally or alternatively, the protrusions extend or project generally parallel to the central axis.

In an embodiment of the prosthesis according to the present disclosure, the free central space has the shape of a cone widening from the distal side of the base portion in a distal direction. It is also possible to design the free central space such that the inner ends of the protrusions diverge from each other when viewed from the distal side of the base portion along the central axis into a distal direction. A tapered shape of the free central space facilitates the fixation of the prosthesis on the humerus bone.

In particular, the protrusions are formed as ribs, blades or fins.

Said protrusions may be in essence planar or curved. It is also possible to combine planar and curved portions to achieve a geometry of the protrusions with the desired properties. Generally, the curvature of the protrusions of embodiments of the prosthesis according to the present disclosure may remain constant or vary along the extension of the protrusions.

In specific embodiments of the prosthesis, an intersection of the protrusions may be contemplated if deemed advantageous as long as the free central space around the central axis is devoid of protrusions of the anchoring means.

The protrusions of the prosthesis may all have similar shapes. However, it may be desirable to provide the prosthesis with protrusions that have different shapes.

It is conceivable that each protrusion defines a plane that includes the central axis. In other words, the planes defined by the protrusions intersect, wherein the intersection of said planes defines the central axis. Alternatively, it may be envisaged to design the protrusions—or at least one of the protrusions—such that their inner ends do not converge towards the central axis. In such a design, inner portions of the protrusions or of their extrapolations may extend—figuratively speaking—tangentially relative to the free central space mentioned above when viewed along the central axis.

In an embodiment of the prosthesis according to the present disclosure, each protrusion has a height measured from the distal side of the base portion, the height of the protrusion increasing or remaining constant from the outer end towards the free central space. In particular, each protrusion has a minimum height at its outer end.

In order to improve the blood circulation in regions of the humerus bone adjacent to the prosthesis and to foster osseointegration, at least one protrusion may be provided with at least one opening.

The process of fixing the prosthesis according to the present disclosure to the humerus bone may be facilitated in case each protrusion comprises a distal edge which is formed at least partly as a cutting edge.

In a further embodiment of the prosthesis according to the present disclosure, at least one pair of neighboring protrusions is connected by a web, wherein the web in particular extends between the inner ends of the protrusions. Said web increases the stability of the prosthesis and contributes to effectively fixing the prosthesis to the humerus bone.

In an embodiment of the prosthesis provided with at least one web as described above, the protrusion and the web may have a height measured from the distal side of the base portion, wherein the height of the web is smaller than the height of the protrusions.

In an embodiment of the prosthesis provided with at least one web, the web is provided with a cutting edge which is in particular provided at a distal edge of the web. In particular, the cutting edge of the web merges into cutting edges of the neighboring protrusions.

In an embodiment of the prosthesis according to the present disclosure, the web is provided with at least one opening in order to e.g. enhance blood circulation in regions adjacent to the prosthesis to foster osseointegration.

In a further embodiment of the prosthesis according to the present disclosure, at least one of or all of the protrusions are provided at their outer ends with wings. In particular, the wings are positioned substantially flush with the base portion on an outer side facing away from the central axis. The wings may extend in substance in tangential directions relative to an outer contour of the prosthesis when viewed along the central axis, giving the protrusions a T-shape in a cross-section parallel to the plane defined by the base portion. Such a T-shaped wing design for the radial outer ends of the protrusions may provide for good stability and support as these wing portions are located relatively near to the border of the resection where a relatively high bone density may be expected. Additionally or alternatively, the inner ends of at least one of or all of the protrusions may be provided with wings as mentioned before in connection with the outer ends of the protrusions. In a cross-section parallel to the base portion, these protrusions may have a dog-bone-like shape.

In an embodiment of the prosthesis according to the present disclosure, the base portion is provided with openings, the openings being arranged between the protrusions.

In an embodiment of the prosthesis according to the present disclosure, the base portion comprises a plate, which may be provided with openings if necessary.

In a further embodiment of the prosthesis according to the present disclosure, the base portion comprises a radially outer ring, a radially inner portion and radial spokes extending between the outer ring and the inner portion. Such a design of the base portion provides good stability while fostering osseointegration. The protrusions may project from the radial spokes. The radially inner portion may have a ring-like shape. Exemplarily, the base portion may have a wheel-like shape.

The outer contour of the base portion may have a circular shape. Alternatively, the base portion may be given an anatomical design which is different from a circular shape. Specifically, the base portion may be given a substantially egg-shaped or pear-shaped design.

Regarding the circumferential direction around the central axis, the protrusions are in specific embodiments arranged at regular intervals. For example, in a design relying on four blades, the blades may be arranged at 90° between every two neighboring blades. Generally, a symmetrical design, in particular if combined with a circular base portion, may be found advantageous.

Alternatively, the plurality of protrusions may be arranged asymmetrically in the circumferential direction. Such an anatomical design, in particular if combined with a non-circular design of the base portion, may make use of the anatomical provisions given at the resected humerus bone. Specifically, it may be taken into account that the bone material below the resection plane does not exhibit a constant bone depth or bone density. Moreover, such an anatomical design may account for the fact that the cross-sections of the resection plane have no symmetry planes.

The number and/or the positioning of the protrusions in such an anatomical design may be chosen in consideration of the mentioned anatomical circumstances in order to obtain reliable support and stability for the prosthesis. The design may or may not be chosen such that the prosthesis is supported predominantly by the cortical bone. Moreover, an anatomical design makes it possible to maximize the cortical coverage for the prosthesis.

Generally, the stemless shoulder prosthesis as disclosed herein may be used in total shoulder arthroplasty as well as in hemi shoulder arthroplasty. Moreover, the disclosed shoulder prosthesis may be used for patients with a so-called dysfunctional rotator cuff.

In addition, the stemless shoulder prosthesis as disclosed herein provides for the general advantages over stemmed prostheses, namely to preserve more bone, to reserve the humeral canal for future arthroplasty and to reduce time and cost of surgery.

In the following, further aspects of the stemless shoulder prosthesis as disclosed herein are described.

The size of the protrusions may increase with increasing size of the prosthesis. However, according to one aspect the size of the base portion may remain constant, i.e. prostheses of different sizes are provided with a uni-sized base portion. This may apply for a symmetrical design having a circular base portion as well as for an anatomical design with a non-circular base portion, in particular having an egg-shaped or pear-shaped base portion design.

As outlined above, some or all of the inner ends of the protrusions may be connected with a web forming a connecting wall. Thereby, a closed wall without circumferential free ends enclosing the free central space may be formed. Alternatively, the wall may be interrupted so as to provide gaps towards the free central space. Specifically, a web may be provided only between some pairs of neighboring protrusions, in particular only within specific groups of protrusions but not between protrusions of different groups.

Generally, said webs may increase the stability or stiffness of the protrusion arrangement and thus of the anchoring means of the prosthesis.

The shape of the protrusions may be that of a non-quadratic and non-rectangular quadrangle with a bottom or proximal side extending parallel to the base portion and a top or distal side extending from an inner position under an angle to the central axis towards an outer position. Thus, the plurality of protrusions together may form an arrow-like design, with the tip of the arrow lying on the central axis of the prosthesis. An inverse design, in which the distal edges of the protrusions recede towards the base portion from outwards to inwards, is also conceivable.

Further embodiments of the disclosure are also recited in the dependent claims, the description and the drawings.

The different embodiments of the stemless shoulder prosthesis described above in accordance with the scope of the independent claim(s) and the features realized there and/or recited in the dependent claims of this disclosure may be combined.

Further areas of applicability of the present disclosure will become apparent from the detailed description provided hereinafter. It should be understood that the detailed description and specific examples are intended for the purpose of illustration only and are not intended to limit the scope of the invention in any way. The figures are simplified and schematic. Details not necessary for the understanding of the invention are omitted.

Figure 7:
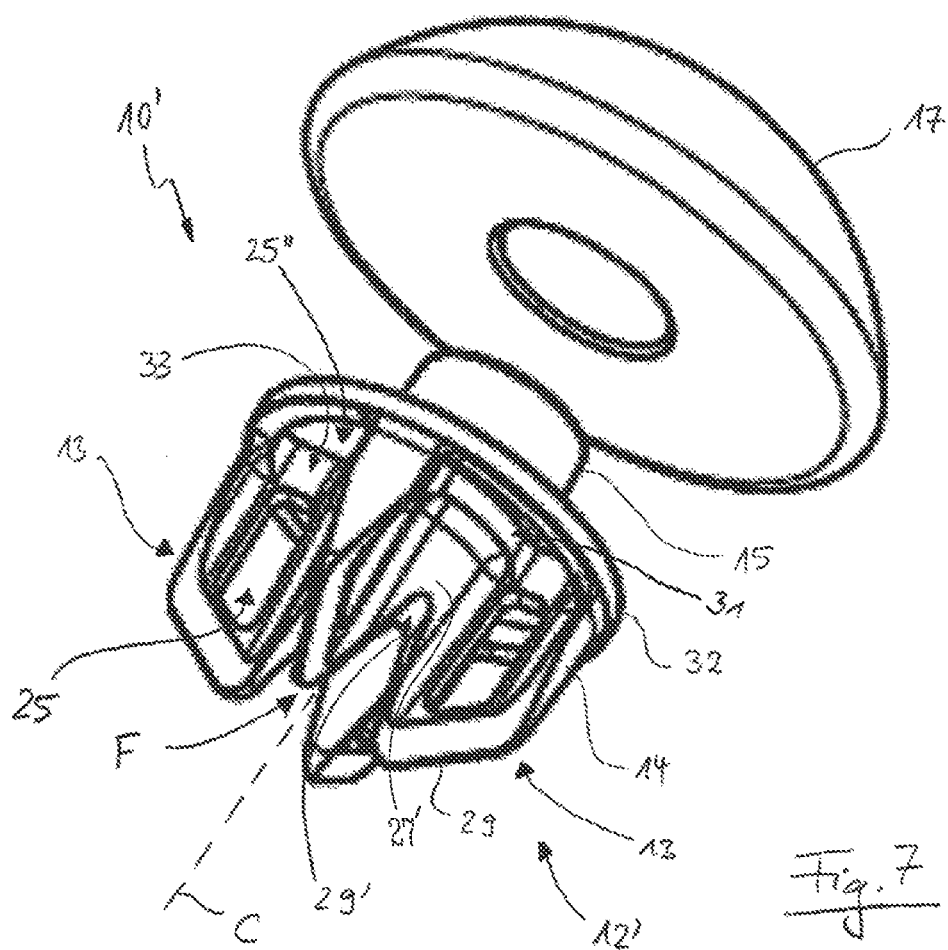
Figure 10:
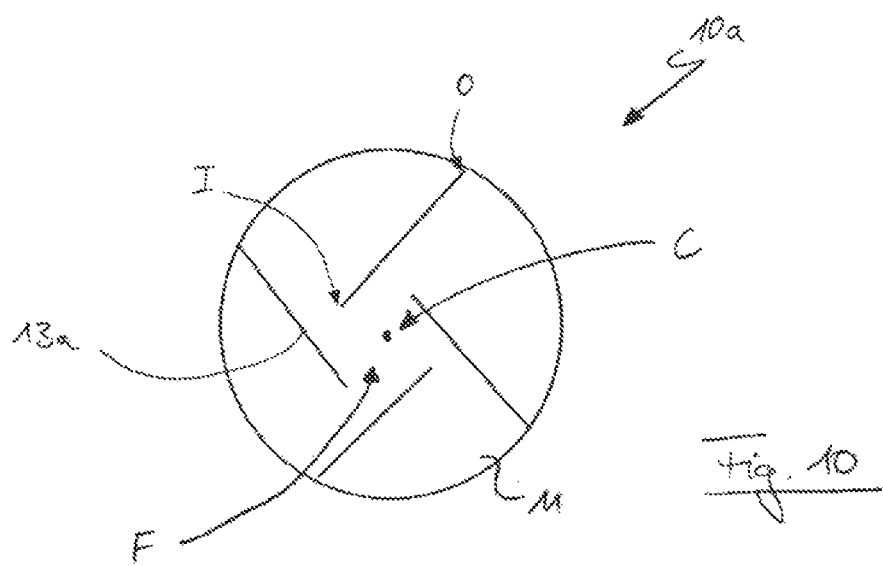
Figure 11:
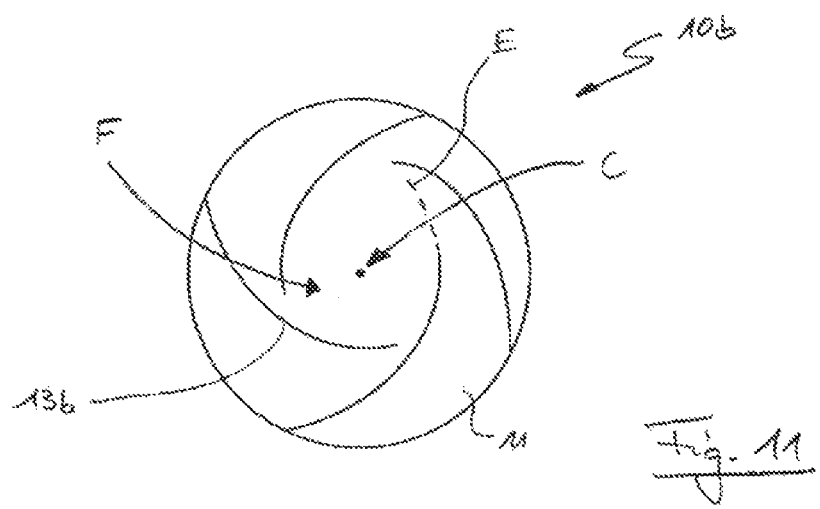
Figure 12:
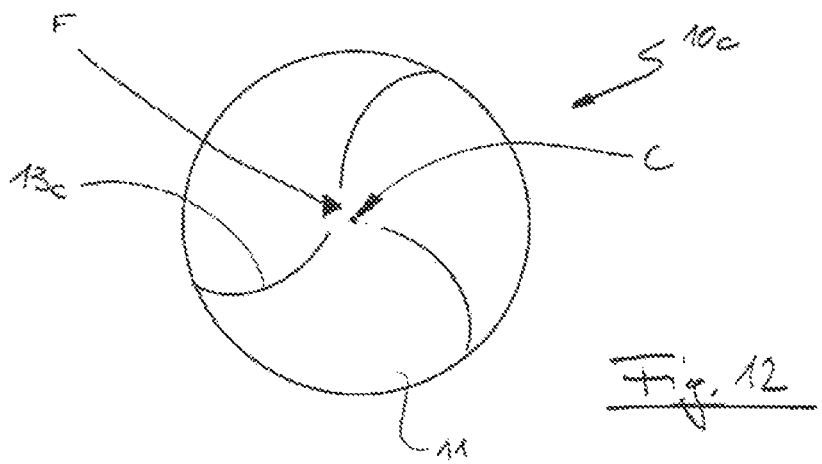

The present disclosure will be explained in more detail and becomes fully understood from the detailed description and the accompanying drawings, wherein FIGS. 1 to 6 show a first embodiment of a stemless shoulder prosthesis according to the present disclosure, FIGS. 7 to 9 show a second embodiment of a stemless shoulder prosthesis according to the present disclosure, and FIGS. 10 to 12 show schematic representations of further embodiments of a stemless shoulder prosthesis according to the present disclosure.

Figure 2:
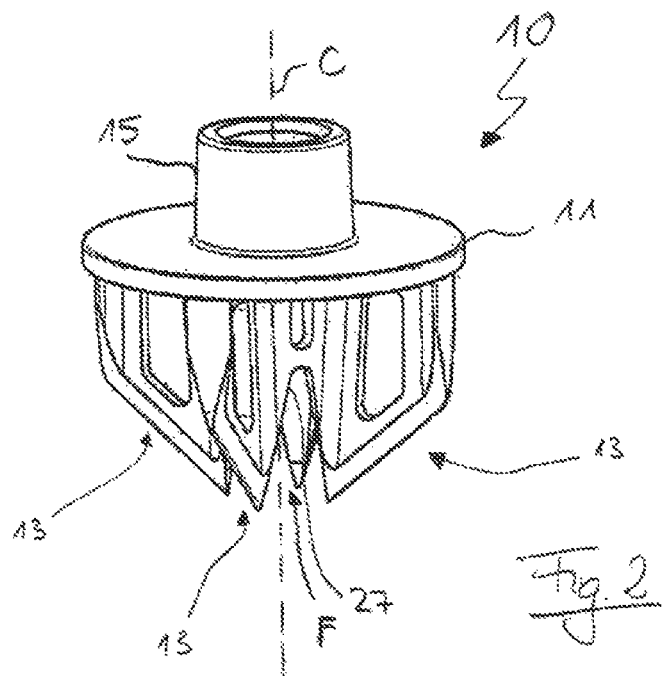

FIGS. 1 and 2 show a stemless shoulder prosthesis 10 according to the present disclosure having a symmetrical design from different perspectives.

Prosthesis 10 comprises a circular base plate 11 provided with a connection portion 15 which allows attaching a prosthetic humeral head (not shown) to prosthesis 10. Instead of slightly tapered connection portion 15, any other suitable connection means may be used to reliably connect the humeral head to prosthesis 10.

The distal side of base plate 11 is provided with anchoring means 12 that serve to reliably anchor prosthesis 10 in the humerus bone of a patient. Anchoring means 12 comprises four ribs or blades 13 extending perpendicularly from base plate 11. Blades 13 are in essence planar and are evenly distributed in a circumferential direction around central axis C, i.e. an angle between neighboring blades 13 is 90°. However, more or less blades 13 may be provided. Further, an even distribution of blades 13 is not imperative. Blades 13 extend in essence exclusively in a radial direction, i.e. each blade 13 defines a plane which extends perpendicular to the base plate 11 and includes the central axis C.

The radially inner ends I of neighboring blades 13 are connected by webs 27 having a significantly smaller extension in a distal direction compared to blades 13. Webs 27 enclose a region adjacent to plate 11 of free central space F around central axis C which is free of protrusions. Therefore, in an implanted state of prosthesis 10 material of the humerus bone extends into space F promoting osseointegration. To foster this process, webs 27 are provided with openings 25' which—inter alia—improve the blood circulation in regions adjacent to prosthesis 10. In particular, openings 25' allow said circulation in a radial direction into and out of the bony material disposed in free central space F.

For similar reasons, blades 13 are provided with openings 25. They improve the blood circulation—and thus osseointegration—in a circumferential direction. Moreover, providing openings 25, 25' and space F minimizes the size of prosthesis 10 thereby minimizing the surgical impact of the implant while at same time promoting its osseointegration properties.

The radially outer ends O of blades 13 are provided with wings 14 that extend in essence in a circumferential direction. Wings 14 are disposed in essence flush with the outer contour of base plate 11. Wings 14 improve the anchoring properties of blades 13 and contribute—as webs 27—to the stability and stiffness of prosthesis 10.

The distal edge of wings 14 and blades 13 form a cutting edge 29 facilitating the implantation of prosthesis 10. In contrast, the distal edges of webs 27 are in this exemplary embodiment not provided with a cutting edge.

The geometry of blades 13 is such that prosthesis 10 resembles in a side view the shape of an arrow head, i.e. the distal edges of blades 13 essentially recede in a radial direction towards the radially outer end O of blades 13. The edges of radially inner ends I of blades 13 are inclined with respect to central axis C. In other words, the radially inner edges of blades 13 diverge when viewed along central axis C from a distal surface of base plate 11, i.e. when viewed from proximal to distal. Free central space F has therefore a conical shape tapering towards base plate 11.

FIG. 3 shows a view of prosthesis along central axis C from distal. It can be seen that wings 14 give the radially outer ends O of blades 14 a T-shape. FIG. 3 also indicates the positioning of cross-section A-A shown in FIG. 4.

The cross-section of FIG. 4 shows the conical shape of free central space F which is devoid of protrusions that contribute to the anchoring properties of anchoring means 12. Moreover, it can be seen that connection portion 15 is provided with a bore 28 to facilitate the reliable fixation of a humeral head to portion 15.

FIGS. 5 and 6 show different side views of prosthesis 10 to visualize the relative proportions of its functional components. Of course, these proportions may be varied to provide a set of prostheses of different sizes and/or to provide prostheses optimized as regards patient specific needs. Further, it can be seen how U or V-shaped distal edges of webs 27 merge with the radially inner edges of blades 13.

FIG. 7 shows a perspective view of a stemless shoulder prosthesis 10'—which is in many aspects similar to prosthesis 10—and a humeral head 17 to be attached to prosthesis 10' via connection portion 15. However, there are some differences between prostheses 10, 10'.

E.g. webs 27' connecting blades 13' of anchoring means 12' of prosthesis 10' are on the one hand not provided with openings (cf. openings 25' of webs 27 of prosthesis 10), on the other hand webs 27' are provided with a cutting edge 29' that merges with cutting edges 29 of adjoining blades 13'. Moreover, the openings 25 of blades 13' are somewhat larger than openings 25 of blades 13. Further, although anchoring means 12' also resemble the shape of a head of an arrow, the slope of the distal edges of blades 13' is less pronounced and the transition between the distal edges and the edges of radially outer ends O of blades 13' and the transition between the distal edges and the edges of radially inner ends I of blades 13' are smoother.

Another difference relates to the design of the base portion of prosthesis 10'. It is not of plate-like design but is formed by an inner portion 31 and an outer ring 32. Portion 31 and ring 32 are connected by radial spokes 33 thereby delimiting openings 25". Blades 13' project from spokes 33.

This design is sufficiently stiff and stable and at the same time promotes osseointegration while being of reduced weight compared to prosthesis 10. The aspects described above are also revealed by FIG. 8 and the central drawing of FIG. 9 which depict prosthesis 10' as seen along central axis C from proximal and from distal, respectively.

The further drawings of FIG. 9 showing side views of prosthesis 10' underline that prosthesis 10' has a rotational symmetry with respect to central axis C.

FIGS. 10 to 12 depict schematically further embodiments 10a, 10b, 10c of a stemless shoulder prosthesis according to the present disclosure. Said figures show a view along central axis C from distal.

FIG. 10 shows a prosthesis 10a with planar protrusions 13a. Even if extrapolated, protrusions 13a do not extend into free central space F. The planes defined by protrusions 13a do not intersect in central axis C. Hence, radially outer ends O and radially inner ends I of protrusions 13a do not lie on a radial line in contrast to the design of protrusions 13, 13' of prosthesis 10, 10', respectively, described above. However, in embodiments 10, 10' and 10a—and in the embodiments described further below—inner ends I are located closer to central axis C than outer ends O. Figuratively speaking, protrusions 13a pass central space F tangentially.

FIG. 11 shows a prosthesis 10b with curved protrusions 13b. The curvature, however, does not result in a convergence of the extrapolation E of the extension of protrusions 13b— indicated by a dashed line extrapolating the radially inner extension of one of protrusions 13b—into central space F. Protrusions 13b pass free central space F tangentially or—figuratively speaking wind around free central space F without intersecting each other.

FIG. 12 shows a prosthesis 10c which is provided with curved protrusions 13c as well. Here, the curvature and the positioning of protrusions 13c is such that their extrapolations (not shown) converge into free central space F without intersecting in central axis C. It may be envisaged, however, to adapt the curvature and/or the positioning of protrusions 13c to achieve an intersection of their extrapolations in central axis C.

All anatomical terms relating to directions and locations, such as anterior, posterior, medial, lateral, proximal, distal and sagittal, refer to an intended implanted state of the components and implants described above.

The description is merely of exemplary nature and, thus, variations that do not depart from the gist of the disclosed teachings are intended to be within the scope of the disclosure.

LIST OF REFERENCE NUMBERS 10, 10', 10a, 10b, 10c prosthesis
11 base plate
12, 12' anchoring means
13, 13', 13a, 13b, 13c rib, blade
14 wing
15 connection portion
17 humeral head
25, 25', 25" opening
27, 27' web
28 bore
29, 29' cutting edge
31, 32 ring
33 spoke
C central axis
F free central space
I inner end
O outer end
E extrapolation

The invention claimed is:

1. Stemless shoulder prosthesis comprising a fixation device for fixing the prosthesis to a resected humerus bone,
the fixation device comprising a base portion and anchoring means, the base portion having a distal side adapted to contact a resection plane of the bone and a proximal side for carrying a humeral head, and the anchoring means being connected to the distal side of the base portion and adapted to fix the prosthesis to the bone,
wherein the anchoring means define a central axis,
wherein the anchoring means comprise a plurality of protrusions projecting from the base portion, each protrusion extending between an inner end and an outer end, the inner end being closer to the central axis than the outer end; and
wherein the protrusions define a free central space around the central axis and,
wherein the protrusions are provided at their outer ends with wings.

2. Stemless shoulder prosthesis according to claim 1, wherein the inner ends of the protrusions define the free central space.

3. Stemless shoulder prosthesis according to claim 1, wherein the free central space has the shape of a cone widening from the distal side of the base portion and/or wherein the inner ends of the protrusions diverge from each other.

4. Stemless shoulder prosthesis according to claim 1, wherein the protrusions are formed as ribs, blades or fins.

5. Stemless shoulder prosthesis according to claim 1, wherein each protrusion has a height measured from the distal side of the base portion, the height of the protrusion increasing or remaining constant from the outer end towards the free central space, in particular wherein each protrusion has a minimum height at its outer end.

6. Stemless shoulder prosthesis according to claim 1, wherein at least one protrusion is provided with at least one opening.

7. Stemless shoulder prosthesis according to claim 1, wherein each protrusion comprises a distal edge which is formed at least partly as a cutting edge.

8. Stemless shoulder prosthesis according to claim 1, wherein at least one pair of neighboring protrusions is connected by a web, wherein the web extends between the inner ends of the protrusions.

9. Stemless shoulder prosthesis according to claim 1, wherein the base portion has openings, the openings being arranged between the protrusions.

10. Stemless shoulder prosthesis according to claim 1, wherein the base portion comprises a plate.

11. Stemless shoulder prosthesis comprising a fixation device for fixing the prosthesis to a resected humerus bone,
the fixation device comprising a base portion and anchoring means, the base portion having a distal side adapted to contact a resection plane of the bone and a proximal side for carrying a humeral head, and the anchoring means being connected to the distal side of the base portion and adapted to fix the prosthesis to the bone,
wherein the anchoring means define a central axis,
wherein the anchoring means comprise a plurality of protrusions projecting from the base portion, each protrusion extending between an inner end and an outer end, the inner end being closer to the central axis than the outer end; and
wherein the protrusions define a free central space around the central axis,
wherein at least one pair of neighboring protrusions is connected by a web, wherein the web extends between the inner ends of the protrusions,
wherein the web is provided with a cutting edge,
and wherein the cutting edge of the web merges into cutting edges of the neighboring protrusions.

12. Stemless shoulder prosthesis according to claim 11, wherein the protrusions and the web have a height measured from the distal side of the base portion, the height of the web being smaller than the height of the protrusions.

13. Stemless shoulder prosthesis according to claim 11, wherein the web is provided with at least one opening.

14. Stemless shoulder prosthesis according to claim 11, wherein the protrusions are provided at their outer ends with wings.

15. Stemless shoulder prosthesis comprising a fixation device for fixing the prosthesis to a resected humerus bone,
the fixation device comprising a base portion and anchoring means, the base portion having a distal side adapted to contact a resection plane of the bone and a proximal side for carrying a humeral head, and the anchoring means being connected to the distal side of the base portion and adapted to fix the prosthesis to the bone, wherein the anchoring means define a central axis, wherein the anchoring means comprise a plurality of protrusions projecting from the base portion, each protrusion extending between an inner end and an outer end, the inner end being closer to the central axis than the outer end; and wherein the protrusions define a free central space around the central axis, and wherein the base portion comprises a radially outer ring, a radially inner portion and radial spokes extending between the outer ring and the inner portion.

16. Stemless shoulder prosthesis according to claim 15, wherein each protrusion extends radially from the outer end to the inner end.

17. Stemless shoulder prosthesis according to claim 15, wherein the inner ends of the protrusions define the free central space.

18. Stemless shoulder prosthesis according to claim 15, wherein the free central space has the shape of a cone widening from the distal side of the base portion and/or wherein the inner ends of the protrusions diverge from each other.

19. Stemless shoulder prosthesis according to claim 15, wherein the protrusions are formed as ribs, blades or fins.

20. Stemless shoulder prosthesis according to claim 15, wherein each protrusion has a height measured from the distal side of the base portion, the height of the protrusion increasing or remaining constant from the outer end towards the free central space, in particular wherein each protrusion has a minimum height at its outer end.

* * * * *